Figure 1:
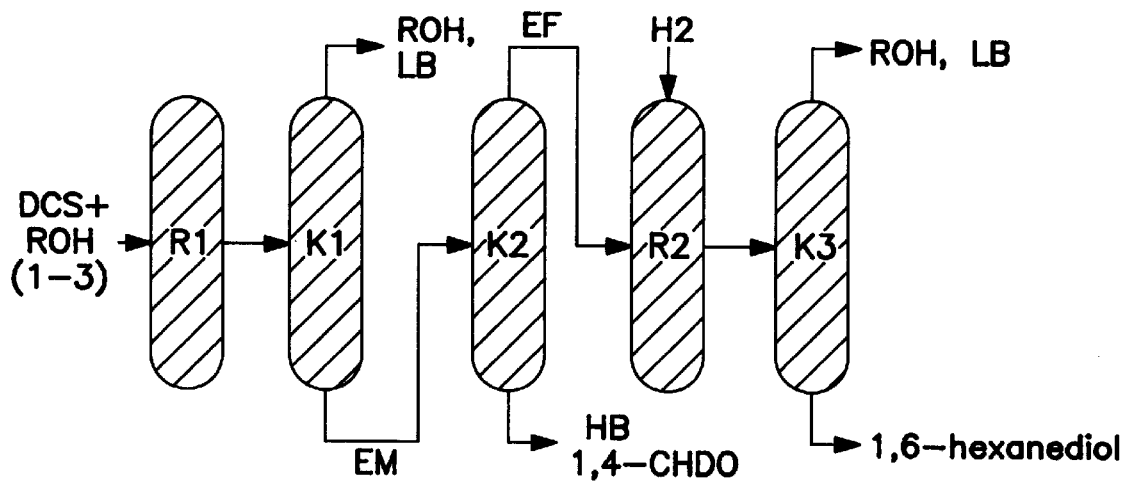

United States Patent [19]

Baur et al.

[11] Patent Number: 6,008,418
[45] Date of Patent: Dec. 28, 1999

[54] PROCESS FOR PREPARING 1,6 HEXANEDIOL WITH A LEVEL OF PURITY OVER 99%

[75] Inventors: Karl Gerhard Baur, Ludwigshafen; Rolf Fischer, Heidelberg; Rolf Pinkos; Frank Stein, both of Bad Dürkheim; Harald Rust, Neustadt; Boris Breitscheidel, Limburgerhof, all of Germany

[73] Assignee: BASF Aktiengesellschaft, Ludwigshafen, Germany

[21] Appl. No.: 09/125,976

[22] PCT Filed: Feb. 28, 1997

[86] PCT No.: PCT/EP97/00980

§ 371 Date: Aug. 28, 1998

§ 102(e) Date: Aug. 28, 1998

[87] PCT Pub. No.: WO97/31882

PCT Pub. Date: Sep. 4, 1997

[30] Foreign Application Priority Data

Mar. 1, 1996 [DE] Germany .......................... 196 07 955
Nov. 15, 1996 [DE] Germany .......................... 196 47 348

[51] Int. Cl.⁶ .................................................. C07C 31/20
[52] U.S. Cl. ......................... 568/853; 568/852; 568/854; 568/864
[58] Field of Search .................................. 568/852, 853, 568/854, 864; 502/324

[56] References Cited

U.S. PATENT DOCUMENTS

| | | |
|---|---|---|
| 3,350,421 | 10/1967 | Binning . |
| 3,478,112 | 11/1969 | Adam et al. . |
| 3,524,892 | 8/1970 | Horlenko . |
| 3,933,930 | 1/1976 | Dougherty . |
| 5,403,962 | 4/1995 | Schneider ................................ 568/885 |
| 5,406,004 | 4/1995 | Eastland ................................ 568/831 |
| 5,710,349 | 1/1998 | Furusaki ................................ 568/864 |
| 5,767,329 | 6/1998 | Dostalek ................................ 568/852 |

FOREIGN PATENT DOCUMENTS

| | | |
|---|---|---|
| 661 255 | 7/1995 | European Pat. Off. . |
| 673 909 | 9/1995 | European Pat. Off. . |
| 123 5879 | 10/1967 | Germany . |
| 2 060 548 | 6/1972 | Germany . |
| 23 21 101 | 7/1982 | Germany . |
| 28 19 593 | 11/1997 | Germany . |

OTHER PUBLICATIONS

CA:112:178071 abs of JP01249735, Mar. 1988.
CA:118:80490 abs of JP 04202150, Jan. 1990.
CA:118:80489 abs of Jp04202149, Jan. 1990.

*Primary Examiner*—Gary Geist
*Assistant Examiner*—Jean F Vollano
*Attorney, Agent, or Firm*—Keil & Weinkauf

[57] ABSTRACT

1,6-Hexanediol is prepared from a carboxylic acid mixture comprising adipic acid, 6-hydroxycaproic acid and small amounts of 1,4-cyclohexanediols which is obtained as a by-product in the oxidation of cyclohexane to cyclohexanone/cyclohexanol by water extraction of the reaction mixture, by esterification of the acids and hydrogenation wherein a) the monocarboxylic and dicarboxylic acids present in the aqueous dicarboxylic acid mixture are reacted with a low molecular weight alcohol to give the corresponding carboxylic esters, b) the resulting esterification mixture is freed of excess alcohol and low boilers in a first distillation stage, c) the bottoms are fractionated in a second distillation stage to give an ester fraction essentially free of 1,4-cyclohexanediols and a fraction comprising at least the major part of the 1,4-cyclohexanediols, d) the ester fraction essentially free of 1,4-cyclohexanediols is catalytically hydrogenated and e) in a pure distillation stage, 1,6-hexanediol is isolated from the hydrogenation product in a manner known per se.

10 Claims, 2 Drawing Sheets

PROCESS FOR PREPARING 1,6 HEXANEDIOL WITH A LEVEL OF PURITY OVER 99%

This application is the national phase of PCT/EP97/00980, filed Feb. 28, 1997, now WO97/31882.

The present invention relates to a process for preparing 1,6-hexanediol having a purity of at least 99% which is, in particular, essentially free of 1,4-cyclohexanediols, from a carboxylic acid mixture which is obtained in the oxidation of cyclohexane to cyclohexanone/cyclohexanol using oxygen or oxygen-containing gases by water extraction of the reaction mixture, by esterification of the acids, fractionation of the esterification mixture into an ester fraction free of 1,4-cyclohexanediols and a fraction comprising the 1,4-cyclohexanediols, hydrogenation of the ester fraction and purification of the 1,6-hexanediol by distillation.

1,6-Hexanediol is a sought-after monomer building block which is used predominantly in the polyester and polyurethane sector.

The aqueous solutions of carboxylic acids which are formed in the oxidation of cyclohexane to cyclohexanol and cyclohexanone (cf. Ullmann's Encyclopedia of Industrial Chemistry, 5th Edition, 1987, Vol. A8, p. 2/9) as by-products, hereinafter referred to as dicarboxylic acid solution (DCS), generally comprise (calculated in % by weight on an anhydrous basis) from 10 to 40% of adipic acid, from 10 to 40% of 6-hydroxycaproic acid, from 1 to 10% of glutaric acid, from 1 to 10% of 5-hydroxyvaleric acid, from 1 to 5% of 1,2-cyclohexanediols (cis and trans), from 1 to 5% of 1,4-cyclohexanediol (cis and trans), from 2 to 10% by weight of formic acid and also many further monocarboxylic and dicarboxylic acids, oxo and oxa compounds whose individual amounts generally do not exceed 5%. Examples which may be mentioned are acetic acid, propionic acid, butyric acid, valeric acid, caproic acid, oxalic acid, malonic acid, succinic acid, 4-hydroxybutyric and gamma-butyrolactone.

DE 2 321 101 and DE 1 235 879 disclose the hydrogenation of these aqueous dicarboxylic acid solutions at from 120 to 300° C. and pressures of from 50 to 700 bar in the presence of catalysts comprising predominantly cobalt to give 1,6-hexanediol as main product. The hydrogenation products are preferably worked up by distillation. Even with an extremely high distillation efficiency, this work-up succeeds only incompletely, if at all, in separating the 1,4-cyclohexanediols which are unchanged in the hydrogenation from 1,6-hexanediol, so that the 1,4-cyclohexanediols which were initially present in the DCS are still present in the 1,6-hexanediol in a concentration of generally from 2 to 5% by weight.

To counter this problem, some starting points for solutions are known:

U.S. Pat. No. 3,933,930 describes the conversion of 1,4-cyclohexanediol in aqueous solutions of adipic acid and 6-hydroxycaproic acid into cyclohexanol, cyclohexane and/or cyclohexene by catalytically prehydrogenating the mixture. This process requires the use of two different hydrogenation catalysts, one for the prehydrogenation and one for the actual carboxylic acid hydrogenation and is therefore complicated.

In DE A 2 060 548, very pure 1,6-hexanediol is obtained by crystallization. This process too is very complicated and is also associated with considerable yield losses.

A further possible way of obtaining highly pure 1,6-hexanediol is to hydrogenate pure adipic acid or pure adipic esters in place of DCS (K. Weissermel, H. J. Arpe, Industrielle Organische Chemie, VCH-Verlagsgemeinschaft Weinheim, 4th Edition, 1994, page 263). However, pure adipic acid is very expensive in comparison with DCS. In addition, the carboxylic acid mixture obtained in the oxidation of cyclohexane is a waste product which should be utilized in terms of the materials present, for environmental reasons too.

It is an object of the present invention to develop a novel process in which 1,6-hexanediol can be obtained in high purity, in high yield and with justifiable outlay from DCS.

We have found that this object is achieved by a process for preparing 1,6-hexanediol from a carboxylic acid mixture comprising adipic acid, 6-hydroxycaproic acid and small amounts of 1,4-cyclohexanediols which is obtained as a by-product in the oxidation of cyclohexane to cyclohexanone/cyclohexanol using oxygen or oxygen-containing gases by water extraction of the reaction mixture, by esterification of the acids and hydrogenation wherein a) the monocarboxylic and dicarboxylic acids present in the aqueous dicarboxylic acid mixture are reacted with a low molecular weight alcohol to give the corresponding carboxylic esters, b) the resulting esterification mixture is freed of excess alcohol and low boilers in a first distillation stage, c) the bottoms are fractionated in a second distillation stage to give an ester fraction essentially free of 1,4-cyclohexanediols and a fraction comprising at least the major part of the 1,4-cyclohexanediols, d) the ester fraction essentially free of 1,4-cyclohexenediols is catalytically hydrogenated and e) in a pure distillation stage, 1,6-hexanediol is isolated from the hydrogenation product in a manner known per se.

It is surprising that in the separation of the ester mixtures which are formed by esterification of the monocarboxylic and dicarboxylic acids present in the DCS, the 1,4-cyclohexanediols, which can of course likewise be present as esters of carboxylic acids, can be separated off in such a way that after hydrogenation and work-up the remaining very low 1,4-cyclohexanediol content of the 1,6-hexanediol is no longer of any practical importance. Owing to the complicated mixtures to be separated, it is surprising that it has been possible to remove the 1,4-cyclohexanediols or their esters virtually completely from the $C_6$-esters used for the hydrogenation to 1,6-hexanediol despite the unfavorable boiling point relationships and danger of azeotrope formation.

The esterification can be carried out without addition of catalysts, or preferably in the presence of catalysts. Suitable low molecular weight alcohols are generally those having from 1 to 10 carbon atoms, in particular alkanols having from 1 to 8 carbon atoms. Diols such as butanediol or pentanediol are also suitable in principle.

The industrially preferred alcohols used for the esterification are n- or i-butanol and in particular methanol.

In the case of the esterification using methanol (variant A), the procedure is to obtain, in the distillation stage (c), a methyl carboxylate fraction essentially free of 1,4-cyclohexanediols at the top of the column and a fraction comprising the high boilers and the 1,4-cyclohexanediols as bottoms and to catalytically hydrogenate the methyl carboxylate fraction in the hydrogenation state (d).

If n- or i-butanol is used for the esterification (variant B), the 1,4-cyclohexanediols together with the low boilers are separated off at the top in the distillation stage (c) and the butyl carboxylates are obtained as a side stream or as bottoms comprising these and are subsequently introduced into the hydrogenation stage (d). The process of the present invention and its variants A (FIG. 1) and B (FIG. 2) are explained in general as follows (where the term at the top means that the offtake is above the feed point and as bottoms means that the offtake is below the feed point):

Variant A

As shown in FIG. 1, the dicarboxylic acid solution (DCS), if desired after dewatering, is fed together with a $C_1$–$C_3$-alcohol, preferably methanol, into the esterification reactor $R_1$ in which the carboxylic acids are esterified. The esterification mixture obtained then goes to the column $K_1$ in which the excess alcohol (ROH), water and low boilers (LB) are distilled off at the top and the ester mixture (EM) is taken off as bottoms and is fed into the fractionation column $K_2$. In this column, the mixture is fractionated into an ester fraction (EF) essentially free of 1,4-cyclohexanediols and a bottoms fraction comprising high boilers (HB) and 1,4-cyclohexanediols (1,4-CHDO). The ester fraction (EF) is then catalytically hydrogenated in the hydrogenation reactor $R_2$ and the hydrogenation mixture is fractionated in the distillation colomn $K_3$ to give alcohol (ROH), low boilers (LB) and pure 1,6-hexanediol.

Variant B

Figure 2:
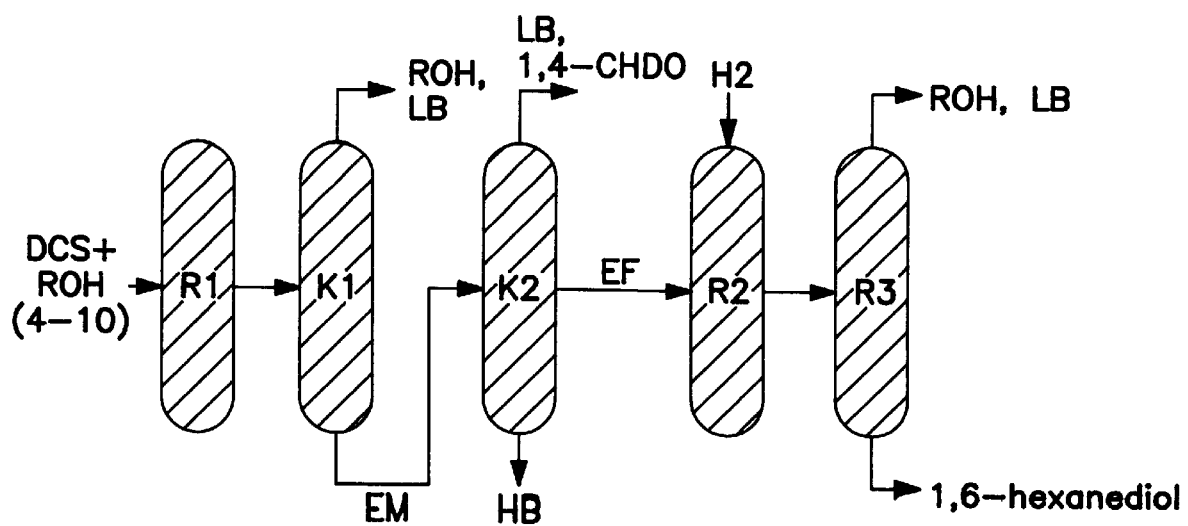

If alcohols having 4 or more carbon atoms, in particular n- or i-butanol, are used for the esterification, the process as shown in FIG. 2 differs only in that in the fractionation column $K_2$ the ester mixture (EM) is fractionated to give a top product of low boilers (LB) in which the 1,4-cyclohexanediols (1,4-CHDO) are present and an ester fraction (EF) essentially free of 1,4-cyclohexanediol which is obtained as a side fraction or as bottoms comprising the ester fraction and is fed into the hydrogenation stage ($R_2$).

Figure 3:
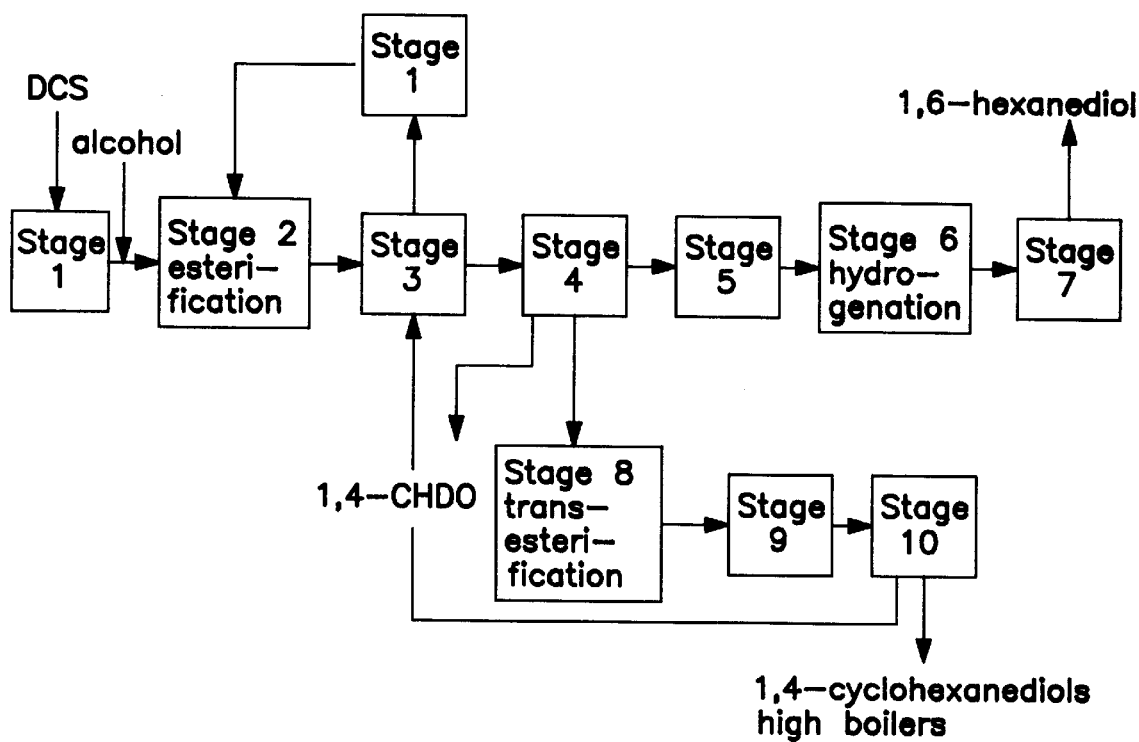

The process of the present invention is explained in detail below. As shown in FIG. 3, the individual process steps are classified into further stages, where the stages 2, 3, 4, 5, 6 and 7 are essential to the process and the stages 3 and 4 as well as 6 and 7 may be combined. The stages 8, 9, 10 and 11 are not strictly necessary, but may be useful for improving the economics of the process.

The dicarboxylic acid solution (DCS) is generally an aqueous solution having a water content of from 20 to 80%. Since an esterification reaction is an equilibrium reaction, it is usually useful, particularly in an esterification using, for example, methanol, to remove water present prior to the reaction, especially when water cannot be removed during the esterification reaction, eg. cannot be removed as an azeotrope. The dewatering in stage 1 can be carried out, for example, using a membrane system or preferably by means of a distillation apparatus in which water is removed at the too at from 10 to 250° C., preferably from 20 to 200° C., particularly preferably from 30 to 200° C., and a pressure of from 1 to 1500 mbar, preferably from 5 to 1100 mbar, particularly preferably from 20 to 1000 mbar, and higher monocarboxylic acids, dicarboxylic acids and 1,4-cyclohexanediols are taken off as bottoms. The bottom temperature is here preferably selected such that the bottom product can be taken off in liquid form. The water content at the bottom of the column can be from 0.01 to 10% by weight, preferably from 0.01 to 5% by weight, particularly preferably from 0.01 to 1% by weight.

The removal of the water can be carried out such that the water is obtained substantially free of acid or the lower monocarboxylic acids present in the DCS, essentially formic acid, can be mostly distilled off with the water so that they do not bind any esterification alcohol in the esterification.

An alcohol having from 1 to 10 carbon atoms is mixed into the carboxylic acid stream from stage 1: in the case of variant A an alcohol having from 1 to 3 carbon atoms, viz. methanol, ethanol, propanol or isopropanol, preferably methanol, in the case of variant B an alcohol having from 4 to 10, in particular from 4 to 8, carbon atoms and particularly preferably n-butanol, iso-butanol, n-pentanol and i-pentanol.

The mixing ratio of alcohol to carboxylic acid stream (mass ratio) can be from 0.1 to 30, preferably from 0.2 to 20, particularly preferably from 0.5 to 10.

This mixture goes as melt or solution into the reactor of stage 2 in which the carboxylic acids are esterified with the alcohol. The esterification reaction can be carried out at from 50 to 400° C., preferably from 70 to 300° C., particularly preferably from 90 to 200° C. External pressure can be applied, but the esterification is preferably carried out under the intrinsic pressure of the reaction system. The esterification apparatus used can be a stirred reactor or a flow tube or a plurality of each these can be used. The residence time necessary for the esterification is from 0.3 to 10 hours, preferably from 0.5 to 5 hours. The esterification reaction can proceed without addition of a catalyst, but a catalyst is preferably added to increase the reaction rate. This can be a homogeneously dissolved or a solid catalyst. Examples of homogeneous catalysts are sulfuric acid, phosphoric acid, hydrochloric acid, sulfonic acids such as p-toluenesulfonic acid, heteropolyacids, such as tungstophosphoric acid or Lewis acids such as aluminum, vanadium, titanium and boron compounds. Preference is given to mineral acids, in particular sulfuric acid. The weight ratio of homogeneous catalyst to carboxylic acid melt is generally from 0.0001 to 0.5, preferably from 0.001 to 0.3.

Suitable solid catalysts are acid or superacid materials, eg. acid and superacid metal oxides such as $SiO_2$, $Al_2O_3$, $SnO_2$, $ZrO_2$ or sheet silicates or zeolites, which can all be doped with mineral acid radicals such as sulfate or phosphate to increase the acidity, or organic ion exchangers containing sulfonic acid or carboxylic acid groups. The solid catalysts can be used in a fixed bed or as a suspension.

The water formed in the reaction is advantageously removed continuously, eg. by means of a membrane or by distillation.

The completeness of the conversion of the free carboxyl groups present in the carboxylic acid melt is determined by means of the acid number (mg KOH/g) measured after the reaction. It is, with subtraction of any acid added as catalyst, from 0.01 to 50, preferably from 0.1 to 10. Not all of the carboxyl groups present in the system are present as an ester of the alcohol used, but some of them can be present in the form of dimeric or oligomeric esters, eg. with the OH end of the hydroxycaproic acid.

The esterification mixture is fed to stage 3, a membrane system or preferably a distillation column. If a dissolved acid has been used as catalyst for the esterification reaction, the esterification mixture is advantageously utilized with a base, with from 1 to 1.5 equivalents of base being added per acid equivalent of the catalyst. As bases, use is generally made of alkali metal or alkaline earth metal oxides, carbonates, hydroxides or alkoxides, or amines, as such or dissolved in the esterification alcohol.

If a column is used in stage 3, the feed to the column is preferably between the top and bottom streams. At the top, the excess esterification alcohol ROH, water and, for example, corresponding esters of formic acid, acetic acid and propionic acid are taken off at from 0 to 150° C., preferably from 15 to 90° C. and in particular from 25 to 75° C., and pressures of from 1 to 1500 mbar, preferably from 20 to 1000 mbar, particularly preferably from 40 to 800 mbar. This stream can either be incinerated or preferably be worked up further in stage 11.

The bottom product obtained is an ester mixture consisting predominantly of the esters of the alcohol ROH used with dicarboxylic acids such as adipic acid and glutaric acid, hydroxycarboxylic acids such as 6-hydroxycaproic acid and 5-hydroxyvaleric acid, and also of oligomers and free or esterified 1,4-cyclohexanediols. It can be useful to allow an amount of water and/or alcohol ROH of up to 10% by weight of each to remain in the ester mixture. The bottom temperatures are from 70 to 250° C., preferably from 80 to 220° C., particularly preferably from 100 to 190° C.

The stream from stage 3, which has been largely freed of water and esterification alcohol ROH, is fed to stage 4. The latter is a distillation column in which the feed is generally between the low-boiling components and the high-boiling components. The column is operated at from 10 to 300° C., preferably from 20 to 270° C., particularly preferably from 30 to 250° C., and pressures of from 1 to 1000 mbar, preferably from 5 to 500 mbar, particularly preferably from 10 to 200 mbar.

In variant A, ie. the esterification using $C_1$–$C_3$-alcohols, in particular methanol, the stream from stage 3 is then separated into a top fraction to be hydrogenated and a bottoms fraction comprising the 1,4-cyclohexanediols.

The top fraction consists predominantly of remaining water and remaining alcohol ROH, esters of the alcohol ROH with monocarboxylic acids, predominantly $C_3$–$C6$-monocarboxylic acids, esters with hydroxycarboxylic acids such as 6-hydroxycaproic acid and 5-hydroxyvaleric acid, and also, in particular, the diesters with dicarboxylic acids such as adipic acid, glutaric acid and succinic acid, also 1,2-cyclohexanediols, caprolactone and valerolactone.

The components mentioned can be taken off together at the top and introduced into the hydrogenation (stage 5) or, in a further preferred embodiment, fractionated in the column into a top stream comprising predominantly remaining water and remaining alcohol plus the abovementioned esters of the $C_3$–$C_5$-carboxylic acids and a side stream comprising predominantly the abovementioned esters of the $C_6$-carboxylic acids and dicarboxylic acids which then go to the hydrogenation.

The high-boiling components of the stream from stage 4, consisting predominantly of 1,4-cyclohexanediols or their esters, dimeric or oligomeric esters as well as sometimes polymeric constituents of the DCS which are not defined in more detail, are separated off in the stripping section of the column. These can be obtained together or in such a way that the 1,4-cyclohexanediols are predominantly separated off via a side stream of the column in the stripping section and the remainder are separated off at the bottom. The 1,4-cyclohexanediols thus obtained can be used, for example, as starting material for active compounds. The high-boiling components, with or without the 1,4-cyclohexanediols, can either be incinerated or, in a preferred embodiment, go to the transesterification in stage 8.

In variant B, ie. the esterification using $C_4$–$C_{10}$-alcohols, in particular n- or i-butanol, the stream from stage 3 can be fractionated in stage 4 into a top fraction comprising the 1,4-cyclohexanediols, a side stream comprising predominantly the $C_6$-esters which goes to the hydrogenation and a bottom stream comprising high boilers which can, if desired, go to stage 8.

The top fraction consists predominantly of remaining alcohol ROH, $C_1$–$C_3$-monoesters of the alcohol ROH, valerolactone and 1,2- and 1,4-cyclohexanediols.

The side stream comprises predominantly diesters of succinic acid, glutaric acid and adipic acid and also monoesters of 5-hydroxyvaleric acid and 6-hydroxycaproic acid. This side stream can be taken off either above or below the feed point of the column and can be introduced into the hydrogenation (stage 5).

The bottom stream comprising oligomeric esters and other high boilers can, in a similar way to variant A, either be incinerated or advantageously go to stage 8.

According to a further embodiment, in stage 4 the $C_6$-esters are separated off together with the bottom stream and then, in a further column, either separated as bottoms from the above-described top fraction which consists predominantly of remaining alcohol ROH, $C_1$–$C_3$-monoesters of the alcohol ROH, valerolactone and 1,2- and 1,4-cyclohexanediols or separated as top stream from the high boilers.

The fraction free or virtually free of 1,4-cyclohexanediols from stage 4, either the total stream or the side stream comprising mainly esters of the $C_6$-acids, is passed to the hydrogenation stage 5.

The stages 3 and 4 can be combined, particularly when only relatively small amounts are being processed. For this purpose, for example, the $C_6$ ester stream can be obtained in a batchwise fractional distillation, again without 1,4-cyclohexanediols getting into the stream fed to the hydrogenation.

The hydrogenation is carried out catalytically either in the gas or liquid phase. Catalysts which can be used are in principle all homogeneous and heterogeneous catalysts suitable for the hydrogenation of carbonyl groups, for example metals, metal oxides, metal compounds or mixtures thereof. Examples of homogeneous catalysts are described, for example, in Houben-Weyl, Methoden der Organischen Chemie, Volume IV/1c, Georg Thieme Verlag Stuttgart, 1980, pp. 45–67 and examples of heterogeneous catalysts are described, for example, in Houben-Weyl, Methoden der Organischen Chemie, Volume IV/1c, pp. 16 to 26.

Preference is given to using catalysts comprising one or more of the elements of transition groups I and VI to VIII of the Periodic Table of the Elements, preferably copper, chromium, molybdenum, manganese, rhenium, ruthenium, cobalt, nickel and palladium, particularly preferably copper, cobalt or rhenium.

The catalysts can consist entirely of the active components or the active components can be applied to supports. Suitable support materials are, for example, $Cr_2O_3$, $Al_2O_3$, $SiO_2$, $ZrO_2$, $ZnO_2$, BaO and MgO or mixtures thereof.

Particular preference is given to catalysts as are described in EP 0 552 463. These are catalysts which, in the oxidic form, have the composition

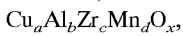

$Cu_aAl_bZr_cMn_dO_x$, where a>0, b>0, c≧0, d>0, a>b/2, b>a/4, a>c and a>d and x is the number of oxygen ions required to maintain electrical neutrality of the formula unit. These catalysts can be prepared, for example, as described in EP 552 463 by precipitation of sparingly soluble compounds from solutions containing the corresponding metal ions in the form of their salts. Suitable salts are, for example, halides, sulfates and nitrates. Suitable precipitants are all agents which lead to formation of insoluble intermediates which can be converted into the oxides by thermal treatment. Particularly suitable intermediates are the hydroxides and carbonates or hydrogencarbonates, so that particularly preferred precipitants are alkali metal carbonates or ammonium carbonate. In the preparation of the catalysts, it is important that the intermediates are thermally treated at from 500° C. to 1000° C. The BET surface area of the catalysts is from 10 to 150 $m^2/g$.

Preference is given to using heterogeneous catalysts which are either used as a fixed bed or as a suspension. If the hydrogenation is carried out in the gas phase and over a fixed-bed catalyst, temperatures of from 150 to 300° C. and pressures of from 1 to 100 bar, preferably from 15 to 70 bar, are generally employed. In this hydrogenation, use is advantageously made of hydrogen as hydrogenating agent and carrier gas in amounts which are at least sufficient for the starting materials, intermediates and products never to become liquid during the reaction. The excess hydrogen is preferably circulated, with it being possible to bleed off a small part as waste gas to remove inerts such as methane. It is possible to use one reactor or a plurality of reactors connected in series.

If the hydrogenation is carried out in the liquid phase using a fixed-bed or suspended catalyst, it is generally carried out at from 100 to 350° C., preferably from 120 to 300° C., and pressures of from 30 to 350 bar, preferably from 40 to 300 bar.

The hydrogenation can be carried out in one reactor or a plurality of reactors connected in series. The hydrogenation in the liquid phase over a fixed bed can be carried out either in the downplow mode or in the upflow mode. According to a preferred embodiment, use is made of a plurality of reactors, with the predominant part of the esters being hydrogenated in the first reactor and the first reactor preferably being operated with circulation of liquid for heat removal and the downstream reactors preferably being operated without circulation to complete the conversion.

The hydrogenation can be carried out batchwise or preferably continuously.

The hydrogenation product consists essentially of 1,6-hexanednol and the alcohol ROH. Further constituents are principally, if the total low-boiling stream from stage 4 of variant A has been used, 1,5-pentanediol, 1,4-butanediol, 1,2-cyclohexanediols and small amounts of monoalcohols having from 1 to 6 carbon atoms and water.

In stage 6, for example a membrane system or preferably a distillation column, this hydrogenation product is fractionated into the alcohol ROH which additionally contains the major part of the further low-boiling components and a stream comprising predominantly 1,6-hexanediol plus 1,5-pentanediol and the 1,2-cyclohexanediols. This is carried out at a pressure of from 10 to 1500 mbar, preferably from 30 to 1200 mbar, particularly preferably from 50 to 1000 mbar, top temperatures of from 0 to 120° C., preferably from 20 to 100° C., particularly preferably from 30 to 90° C., and bottom temperatures of from 100 to 270° C., preferably from 140 to 260° C., particularly preferably from 160 to 250° C. The low-boiling stream can either be recirculated directly to the esterification of stage 2 or go to stage 8 or stage 11.

The 1,6-hexanediol-containing stream is purified in a column in stage 7. In this stage, 1,5-pentanediol, possibly the 1,2-cyclohexanediols and any further low boilers present are separated off at the top. If the 1,2-cyclohexanediols and/or 1,5-pentanediol are to be isolated as additional desired products, they can be separated in a further column. Any high boilers present are removed at the bottom. 1,6-Hexanediol in a purity of at least 99% is taken from the column as a side stream. This purification is carried out at pressures of from 1 to 1000 mbar, preferably from 5 to 800 mbar, particularly preferably from 20 to 500 mbar, top temperatures of from 50 to 200° C., preferably from 60 to 150° C., and bottom temperatures of from 130 to 270° C., preferably from 150 to 250° C.

If only relatively small amounts of 1,6-hexanediol are to be prepared, the stages 6 and 7 can also be combined in a batchwise fractional distillation.

To operate the process of the invention as economically as possible, it is useful to recover the esterification alcohol ROH and to reuse it for the esterification. For this purpose, the stream comprising predominantly the alcohol ROH, for example methanol, from stage 3 and/or 6 can be worked up in stage 11. This is advantageously carried out using a column in which components having boiling points lower than that of the alcohol ROH are removed at the top, water and components having boiling points higher than that of the alcohol ROH are removed at the bottom and the alcohol ROH is isolated as a side stream. The column is advantageously operated at from 500 to 5000 mbar, preferably from 800 to 3000 mbar.

In a further preferred embodiment of the process of the invention, the high-boiling stream from stage 4 (in variant A) is used to increase the total yield of 1,6-hexanediol based on adipic acid and 6-hydroxycaproic acid introduced via the DCS used. For this purpose, the dimeric and oligomerlc esters of adipic acid or hydroxycaproic acid present are reacted in stage 8 with further amounts of the alcohol ROH in the presence of a catalyst. The weight ratio of alcohol ROH and the bottoms stream from stage 4 is from 0.1 to 20, preferably from 0.5 to 10, particularly preferably from 1 to 5. Suitable catalysts are in principle those described above for the esterification in stage 2. However, preference is given to using Lewis acids. Examples of these are compounds or complexes of aluminum, tin, antimony, zirconium or titanium, for example zirconium acetylacetonate or tetraalkyl titanates, eg. tetraisopropyl titanate, which are employed in concentrations of from 1 to 10,000 ppm, preferably from 50 to 6000 ppm, particularly preferably from 100 to 4000 ppm, based on the transesterification mixture. Particular preference is given to titanium compounds.

The transesterification can be carried out batchwise or continuously, in one reactor or a plurality of reactors, in stirred vessels connected in series or tube reactors at from 100 to 300° C., preferably from 120 to 270° C., particularly preferably from 140 to 240° C., and at the intrinsic pressures established. The residence times required are from 0.5 to 10 hours, preferably from 1 to 4 hours.

In the case of the esterification using methanol, this stream from stage 8 can, for example, be returned to stage 3. To avoid accumulations, especially of 1,4-cyclohexanediols, a substream of the high boilers then has to be bled off at intervals or continuously from stage 4. Another possibility is not to recirculate the stream from stage 8 to stage 3 but, in a similar way to stage 3, to fractionate it in a stage 9 into predominantly alcohol ROH, which can then go to stage 2, 8 or 11, and a stream comprising the esters.

This ester stream can in principle (with the proviso that accumulation of the 1,4-cyclohexanediols is avoided) be recirculated to stage 4 or is preferably fractionated in a further stage 10 into the esters of the $C_6$-acids and, relatively unimportant in terms of amount, the esters of the $C_5$-acids on the one hand which are introduced either into stage 4 or directly into stage 5 and, on the other hand, high boilers comprising the 1,4-cyclohexanediols, after which the high boilers are removed from the system.

In this way, yields of 1,6-hexanediol of over 95% can be achieved at purities of over 99%.

The novel process thus allows highly pure 1,6-hexanediol to be obtained in high yield and in an economical manner from a waste product.

The following example illustrates but in no way restricts the process.

EXAMPLE (variant A)

Stage 1 (dewatering)

0.1 kg/h of dicarboxylic acid solution (consisting essentially of adipic acid, 6-hydroxycaproic acid, 1,4-cyclohexanediols, glutaric acid, 5-hydroxyvaleric acid, formic acid, water) were distilled continuously in a distillation apparatus (three-tray bubble cap tray column having an external oil heating circuit, oil temperature=150° C., tray volume=about 25 ml each, feed above the bubble cap trays) having a superposed packed column (about 4 theoretical plates, no runback at the top). The top product obtained comprised 0.045 kg having a formic acid content in water of about 3%. The water content of the bottoms stream (5.5 kg) was about 0.4%.

Stage 2 (esterification)

5.5 kg/h of the bottoms stream from stage 1 were reacted continuously with 8.3 kg/h of methanol and 14 g/h of sulfuric acid in a tube reactor (length 0.7 m, ϕ1.8 cm, residence time 2.7 h) The acid number of the product stream, excluding sulfuric acid, was about 10 mg KOH/g.

Stage 3 (removal of excess alcohol and water)

The esterification stream from stage 2 was distilled in a 20 cm packed column (1015 mbar, 65° C. top temperature to 125° C. bottom temperature). 7.0 kg were taken off at the top. 6.8 kg were obtained as bottoms.

Stage 4 (fractionation; 1,4-cyclohexanediol removal)

The bottoms stream from stage 3 was fractionally distilled in a 50 cm packed column (1 mbar, 70–90° C. too temperature to 180° C. bottom temperature). The bottoms (1.9 kg) contained virtually all the 1,4-cyclohexanediols.

0.6 kg of low boilers was distilled off (1,2-cyclohexanediols, valerolactone, methyl 5-hydroxyvalerate, dimethyl glutarate, dimethyl succinate, etc). 4.3 kg of the fraction comprising predominantly dimethyl adipate and methyl 6-hydroxycaproate were obtained.

The top stream, viz. the ester fraction, is passed to the hydrogenation stage 5.

Stage 5 (hydrogenation)

4.3 kg of the $C_6$-ester fraction from stage 4 were hydrogenated continuously in a 25 ml reactor over a catalyst (catalyst: 70% by weight of CuO, 25% by weight of ZnO, 5% by weight of $Al_2O_3$) which had previously been activated at 180° C. in a stream of hydrogen. The feed was 20 g/h, the pressure 220 bar and the temperature 220° C. The ester conversion was 99.5%, the 1,6-hexanediol selectivity was over 99%.

Alternatively, the ester fraction was hydrogenated continuously in a two-stage reactor cascade (1st reactor: 2.5 l of catalyst, downflow mode, 250 bar, product recirculation: feed=10:1, 220–230° C.; 2nd reactor: 0.5 l of catalyst, downflow mode with straight passage, 260 bar, 220° C.) The catalyst used was a catalyst comprising CuO (60%), $Al_2O_3$ (30%) and $Mn_2O_3$ (10%) which had previously been activated at 180° C. The feed rate was 1 kg/h. At 99.5% conversion, the hexanediol selectivity was over 99%.

Stages 6 and 7

4.0 kg of the hydrogenation product from stage 5 were fractionally distilled (distillation flask with superposed 70 cm packed column, reflux ratio: 2). 1 kg of methanol was distilled off at 1013 mbar. After application of reduced pressure (20 mbar), predominantly the 1,2-cyclohexanediols and 1,5-pentanediol distilled off. Subsequently (bp. 146° C.), 1,6-hexanediol having a purity of 99.8% distilled off. (Remainder predominantly 1,5-pentanediol.)

Stage 8

1.9 kg of the bottom product from stage 4 were admixed with 3.8 kg of methanol and 3.8 g of tetra-i-propyl titanate and reacted continuously in a 1 m long, 440 ml capacity tube reactor which was filled with 3 mm V2A rings. The mean residence time was about 2 hours.

Stage 9

The product from stage 8 was fractionally distilled in an apparatus similar to that described in stage 3. 3.5 kg (predominantly methanol) were distilled off at a top temperature of 65° C. 2.2 kg remained in the bottoms.

Stage 10

The bottoms from stage 9 were fractionally distilled by a method similar to stage 4 to a bottom temperature of 160° C. The distillate obtained comprised 1.3 kg which can be directly hydrogenated or returned to stage 4. Composition: 52% of methyl 6-hydroxycaproate, 31% of dimethyl adipate, 5% of dimethyl glutarate, 4% of methyl 5-hydroxycaproate plus many further components in unimportant amounts.

Stage 11

7 kg of the top product from stage 3 were fractionally distilled at 1015 mbar in a 20 cm packed column. 0.8 kg of a first fraction was obtained at a top temperature of 59–65° C.; this fraction comprised predominantly methanol plus $C_1$–$C_4$-monomethyl esters. At a top temperature of 65° C., 5.6 kg of methanol having a purity of >99% were obtained. The bottoms (0.6 kg) consisted predominantly of water.

We claim:

1. A process for preparing 1,6-hexanediol from an aqueous carboxylic acid mixture comprising adipic acid, 6-hydroxy-caproic acid and small amounts of 1,4-cyclohexanediols, which aqueous carboxylic acid mixture is obtained as a by-product in the oxidation of cyclohexane to cyclohexanone/cyclohexanol using oxygen or oxygen-containing gases followed by water extraction, which process comprises esterifying the aqueous carboxylic acid mixture followed by catalytic hydrogenation, a) reacting monocarboxylic and dicarboxylic acid present in the aqueous carboxylic acid mixture with a low molecular weight alcohol to give an esterification mixture comprising the corresponding carboxylic ester;

b) removing excess alcohol and low boilers from the esterification mixture in a first distillation stage;

c) fractionating bottoms from the first distillation stage in a second distillation stage to give an ester fraction essentially free of 1,4-cyclohexanediols and a fraction comprising at least a major amount of the 1,4-cyclohexanediols;

d) catalytically hydrogenating the ester fraction which is essentially free of 1,4-cyclohexanediols to produce a hydrogenation product; and e) isolating 1,6-hexanediol from the hydrogenation produce in a pure distillation stage.

2. A process as defined in claim 1, wherein the aqueous carboxylic acid mixture is dewatered prior to reaction of monocarboxylic acid and dicarboxylic acid present therein with the low molecular weight alcohol.

3. A process as defined in claim 1, wherein monocarboxylic and dicarboxylic acid present in the aqueous carboxylic acid mixture are reacted with an alkanol having from 1 to 3 carbon atoms.

4. A process as defined in claim 1, wherein monocarboxylic acid and dicarboxylic acid present in the aqueous carboxylic acid mixture are reacted with an alkanol having from 4 to 10 carbon atoms.

5. A process as defined in claim 1, wherein the low molecular weight alcohol is methanol, and in the second distillation stage (c), a methyl carboxylate fraction essentially free of 1,4-cyclohexanediols is obtained at the top of the column and a fraction comprising high boilers and 1,4-cyclohexanediols is obtained as bottoms, and the methyl carboxylate fraction is catalytically hydrogenated in the hydrogenation stage (d).

6. A process as defined in claim 1, wherein the low molecular weight alcohol is n- or i-butanol, and in the second distillation stage (c), the 1,4-cyclohexanediols are separated off at the top together with low boilers, and butyl carboxylates are obtained as a side stream or as bottoms and are catalytically hydrogenated in the hydrogenation stage (d).

7. A process as defined in claim 1, wherein alcohol is isolated in pure form from the product obtained by removing alcohol and low boilers from the esterification mixture in the first distillation stage (b), and this alcohol is recirculated to esterification stage (a).

8. A process as defined in claim 1, wherein bottoms from second distillation stage (c) are subjected at least partially to a renewed esterification by means of further addition thereto of low molecular weight alcohol and an esterification catalyst, followed by removing excess alcohol and low boilers from the renewed esterification in a first distillation stage, then fractionating bottoms from this first distillation stage in a second distillation stage to give a carboxylic ester fraction essentially free of 1,4-cyclohexanediols and a fraction comprising at least a major amount of 1,4-cyclohexanediols, followed by introducing the carboxylic ester fraction into the hydrogenation stage (d).

9. A process as defined in claim 1, wherein the hydrogenation in step (d) is carried out using a catalyst comprising as main catalytically active constituent a member selected from the group consisting of copper, cobalt and rhenium.

10. A process as defined in claim 1, wherein the hydrogenation in stage (d) is carried out using a catalyst which, in the oxidic form, has the composition $Cu_aAl_bZr_cMn_dO_x$, where $a>0$, $b>0$, $c\geqq 0$, $d>0$, $a>b/2$, $b>a/4$, $a>c$ and $a>d$ and x is the number of oxygen ions required to maintain electrical neutrality of the formula unit.

* * * * *